United States Patent
Wolff et al.

(10) Patent No.: US 10,441,698 B2
(45) Date of Patent: Oct. 15, 2019

(54) SUBSTITUTION FLUID PUMP INTEGRATED IN A DIALYSIS MACHINE

(71) Applicant: B. BRAUN AVITUM AG, Melsungen (DE)

(72) Inventors: Henrik Wolff, Witzenhausen (DE); Bjoern Broeker, Staufenberg (DE)

(73) Assignee: B. Braun Avitum AG (DE)

( * ) Notice: Subject to any disclaimer, the term of this patent is extended or adjusted under 35 U.S.C. 154(b) by 607 days.

(21) Appl. No.: 14/734,695

(22) Filed: Jun. 9, 2015

(65) Prior Publication Data

US 2015/0359955 A1 Dec. 17, 2015

(30) Foreign Application Priority Data

Jun. 12, 2014 (DE) .................. 10 2014 108 227

(51) Int. Cl.
- *A61M 1/16* (2006.01)
- *A61M 1/36* (2006.01)
- *A61M 1/34* (2006.01)

(52) U.S. Cl.
CPC ............ *A61M 1/1621* (2014.02); *A61M 1/16* (2013.01); *A61M 1/168* (2013.01); *A61M 1/1682* (2014.02); *A61M 1/3434* (2014.02); *A61M 1/3465* (2014.02); *A61M 1/3601* (2014.02); *A61M 1/3649* (2014.02); *A61M 2205/3337* (2013.01)

(58) Field of Classification Search
CPC .... A61M 1/1621; A61M 1/16; A61M 1/3601; A61M 1/168; A61M 1/3649; A61M 1/3465; A61M 1/3434; A61M 2205/3337
See application file for complete search history.

(56) References Cited

U.S. PATENT DOCUMENTS 4,702,829 A * 10/1987 Polaschegg ......... A61M 1/3413
                                                      210/195.2
7,850,856 B2  12/2010 Zhang et al.
(Continued)

FOREIGN PATENT DOCUMENTS

CN      1692954 A    11/2005
CN    101193670 A  *  6/2008  ........ A61M 1/3627
(Continued)

OTHER PUBLICATIONS

German Search Report for DE 10 2014 108 227.3 dated Mar. 24, 2015.
(Continued)

*Primary Examiner* — Krishnan S Menon
*Assistant Examiner* — Waqaas Ali
(74) *Attorney, Agent, or Firm* — RatnerPrestia

(57) ABSTRACT

A dialysis machine comprising internal fluidics, wherein the internal fluidics includes a dialysis fluid pump for pumping dialysis fluid from a dialysis fluid reservoir through a dialysis fluid feed line to a dialyzer and from the dialyzer through a dialysis fluid drain line to a waste reservoir, a substitution fluid pump for supplying dialysis fluid through a substitution fluid feed line as substitution fluid to an extracorporeal hose system including ports on the patient side and coupling means for connecting the extracorporeal hose system to the internal fluidics is disclosed.

12 Claims, 5 Drawing Sheets

(56) References Cited

U.S. PATENT DOCUMENTS

| | | | |
|---|---|---|---|
| 2006/0200064 A1* | 9/2006 | Gross | A61M 1/16 604/5.01 |
| 2013/0025697 A1 | 1/2013 | Blasek et al. | |
| 2013/0028788 A1 | 1/2013 | Gronau et al. | |
| 2013/0150768 A1* | 6/2013 | Sakamoto | A61M 1/16 604/6.09 |
| 2013/0240443 A1 | 9/2013 | Gronau et al. | |
| 2015/0129498 A1 | 5/2015 | Mishima | |

FOREIGN PATENT DOCUMENTS

| | | | |
|---|---|---|---|
| CN | 103260695 A | 8/2013 | |
| DE | 34 42 744 | 6/1986 | |
| DE | 34 44 671 | 6/1986 | |
| DE | 101 59 620 | 8/2003 | |
| DE | 10 2006 050 272 | 5/2008 | |
| DE | 102010032179 A1 * | 1/2012 | A61M 39/10 |
| DE | 10 2011 108 784 | 1/2013 | |
| DE | 10 2012 004 970 | 9/2013 | |
| EP | 0228160 A2 | 7/1987 | |
| EP | 2 240 218 | 10/2010 | |
| EP | 2 586 474 | 5/2013 | |
| EP | 2 666 491 | 11/2013 | |
| EP | 2 737 915 | 6/2014 | |
| WO | WO 2008/125893 | 10/2008 | |
| WO | WO 2009/074588 | 6/2009 | |
| WO | WO 2012/010322 | 1/2012 | |
| WO | WO 2013/017239 | 2/2013 | |
| WO | WO 2013/180154 | 12/2013 | |

OTHER PUBLICATIONS

European Search Report (with translation) for EP 15 16 8735 dated Mar. 11, 2016.

Chinese Office Action for Chinese Application No. 291510324821.5, dated Jun. 14, 2018; with translation; 14 pages.

\* cited by examiner

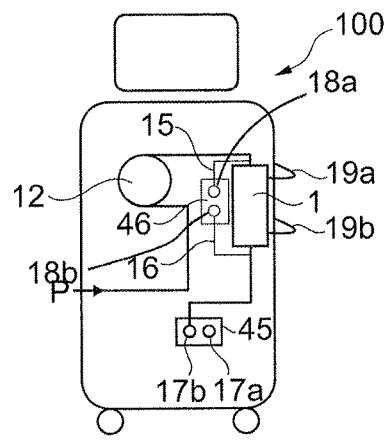
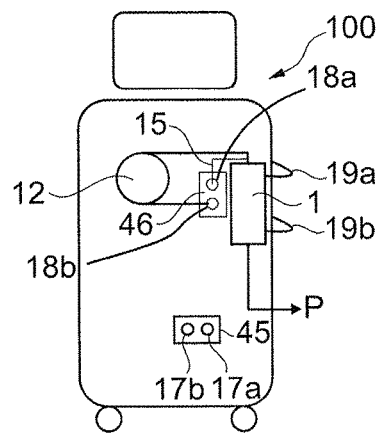
Fig. 10  Fig. 11
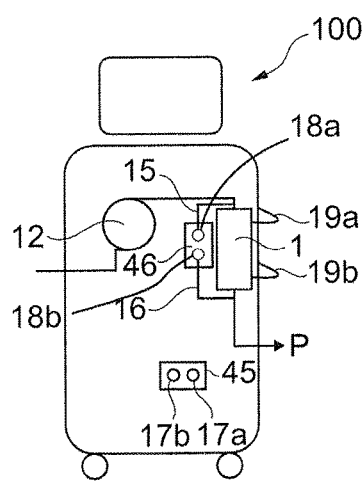
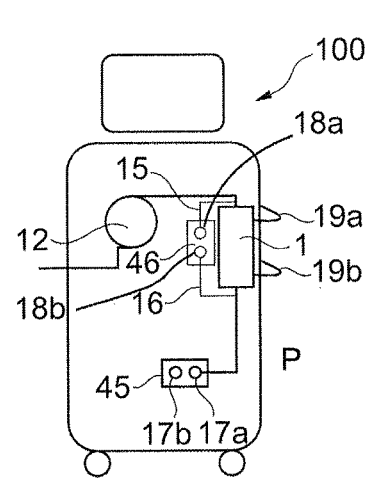
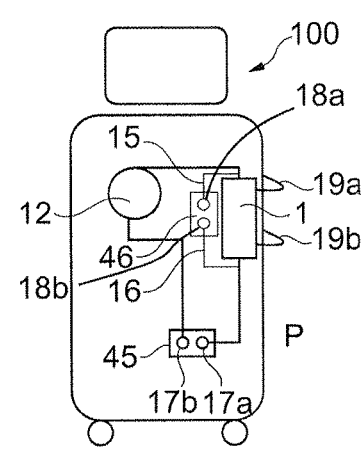
Fig. 12  Fig. 13  Fig. 14

SUBSTITUTION FLUID PUMP INTEGRATED IN A DIALYSIS MACHINE

CROSS REFERENCE TO RELATED APPLICATIONS

This application claims priority to German application DE 10 2014 108 227.3 filed Jun. 12, 2014, the contents of such application being incorporated by reference herein.

FIELD OF THE INVENTION

The invention relates to a dialysis machine comprising internal fluidics, the internal fluidics including the following components:
- a dialysis fluid pump for pumping fresh dialysis fluid from a dialysis fluid reservoir through a dialysis fluid feed line to a dialyzer and to pump used dialysis fluid from the dialyzer through a dialysis fluid drain to a waste reservoir,
- a substitution fluid pump or substitution pump for supplying dialysis fluid through a substitution fluid feed line or substitution feed line as substitution fluid to an extracorporeal hose system including patient-side ports and
- coupling means for connecting the extracorporeal hose system to the internal fluidics.

Furthermore, the invention relates to a dialysis machine comprising internal fluidics, the internal fluidics including the following components:
- a feed line for feeding a fluid to an extracorporeal hose system including patient-side ports and
- a coupling means which is in fluid communication with the feed line to couple a hose line of the extracorporeal hose system to the feed line, the coupling means being arranged to be accessible by the user on a machine front face of the dialysis machine, the dialysis machine including a drain line for draining fluid from the extracorporeal hose system.

BACKGROUND

Basically a dialysis machine includes two fluid systems (fluid circuits), i.e. the so called extracorporeal blood conduit system, also referred to as external fluidics in the present application, and the so called dialysis fluid system, also referred to as internal fluidics, arranged inside the machine (as part of the machine). The extracorporeal blood conduit system and the internal fluidics are in (mass exchange) communication via the dialyzer and the membrane thereof. The extracorporeal blood conduit system is connected via an arterial access and a venous access to the intracorporeal blood circuit of a patient. From the internal fluidics physiological fluid, especially dialysis fluid, can be supplied to the extracorporeal blood conduit system, e.g. for re-supplying large fluid quantities which are deliberately withdrawn from the patient during a dialysis treatment.

DESCRIPTION OF THE RELATED ART

From EP 2 666 491 A1 a hemodialysis apparatus is known comprising permanent and sterilizable internal fluidics and exchangeable single-use external fluidics, wherein the external fluidics includes all blood-side conduits and a dialyzer and the internal fluidics includes the following parts:
- a balancing pump device formed of a dialysis fluid pump and a waste pump coupled thereto, the dialysis fluid pump pumping fresh dialysis fluid from a dialysis fluid source to the dialyzer and the waste pump pumps used dialysis fluid from the dialyzer to a waste destination, and
- a separate substitution fluid pump for pumping fresh dialysis fluid from the dialysis fluid source to the external fluidics.

For connecting the external fluidics to the internal fluidics a substitute coupling (substitution fluid coupling) and dialysis fluid couplings are arranged on the operating side of the hemodialysis apparatus.

From DE 10 2012 004 970 A1 a method of dosing a substitution fluid produced with a blood treatment device as well as a blood treatment device for carrying out the method is known. In the method dosing is carried out with a hydraulic system or a hydraulic section of the blood treatment device. The hydraulic system includes at least one dialysis fluid feed line that opens into a dialysis fluid chamber of a blood filter or a dialyzer or supplies dialysis fluid to the dialyzer. The hydraulic system further includes at least one substitution fluid line as well as a first filtering stage and a second filtering stage.

In known blood treatment devices it is usually a drawback that in the case of change between different forms of therapy, for example hemodialysis (HD), hemofiltration (HF) or hemodiafiltration (HDF), different external fluidics, also referred to as extracorporeal blood or hose systems, have to be connected to the machine. Accordingly, it is complicated and cost-intensive already to hold the different hose systems available. Furthermore, changing or also supplementing the external fluidics bears the problem that sterility and tightness have to be ensured. Especially additional process routines may be required due to a change of external fluidics, such as priming (rinsing the dialyzer at the beginning of therapy), flushing the dialyzer during a therapy, filling the extracorporeal hose system with a patient's blood or re-infusing a patient's blood after a therapy. In total, each variation of the extracorporeal hose system entails relatively high effort.

SUMMARY OF THE INVENTION

Based on the afore-described state of the art, an object underlying the present invention is to eliminate the afore-listed drawbacks, especially to optimize partial dialysis processes, primarily those which require a physiological fluid. Preferably the aptitude of the dialysis machine for being purified and disinfected is to be improved. Moreover, by the dialysis machine preferably different blood treatments are intended to be carried out, wherein the effort in changing the blood treatment should be small and the dialysis machine should be preferably easy to handle.

Under a first aspect of the present invention, this object is achieved by a dialysis machine comprising internal fluidics according to the afore-mentioned definition, the internal fluidics including the following parts/elements:
- a dialysis fluid pump which is adapted to pump dialysis fluid from a dialysis fluid reservoir through a dialysis fluid feed line to a dialyzer and from the dialyzer through a dialysis fluid drain line to a waste reservoir,
- a substitution fluid pump or substitution fluid conveying means adapted to supply dialysis fluid through a substitution fluid feed line (as substitution fluid) to an extracorporeal blood conduit system/hose system including patient-side ports, and
- coupling means adapted to connect the extracorporeal hose system to the internal fluidics.

In accordance with the invention, the internal fluidics of the dialysis machine includes a drain line leading from a coupling means for connecting the extracorporeal hose system to the waste reservoir or waste disposal line.

The drain line is a separate line provided in addition to the dialysis fluid drain. Said separate line includes a separate coupling means at its one end and from there leads directly or indirectly to the waste reservoir. In other words, the drain line is in direct or indirect fluid-connection to the waste reservoir. The dialysis fluid drain equally includes a separate coupling means and likewise leads directly or indirectly to the waste reservoir. Therefore, at the dialysis machine according to aspects of the invention at least two coupling means are provided via which a user can establish a connection from the extracorporeal hose system to the waste reservoir. The dialysis fluid pump can be realized especially by a dialysis fluid feed pump and a dialysis fluid drain pump.

Advantageously, by the dialysis machine under the first aspect of the invention numerous different forms of therapy, such as hemodialysis (HD), hemofiltration (HF) or hemodiafiltration (HDF), can be carried out by external fluidics. The external fluidics can be configured to be equal for all applications, which is especially user-friendly. Further, additional process routines such as priming (rinsing the dialyzer at the beginning of therapy), flushing the dialyzer during therapy, filling the external fluidics with a patient's blood, substitution during HD, HF or HDF, bolus administration during therapy, measuring recirculation, re-infusing a patient's blood after a therapy or preparing the dialyzer for re-use are especially easy to implement. It can be changed between the different substitution forms of pre-dilution and post-dilution as well as mixed dilution explained in detail hereinafter without interrupting the treatment. Finally the external fluidics can be easily emptied after treatment, thus reducing the costs of disposal. It is no longer required to keep at hand the appropriate hose system for the external fluidics for each therapy, which reduces costs and effort. A change between forms of therapy is possible without having to change and reconnect the external fluidics, thus minimizing the risk of poor sterility and tightness. The handling during the preparation of a dialysis is facilitated, sources of error are reduced, costs for additional hose systems or sodium chloride solutions for rinsing the dialyzer are omitted.

An object is achieved, according to a further aspect of the present invention which may possibly be independently claimed, by a dialysis machine comprising internal fluidics according to the definition given at the beginning, the internal fluidics including the following parts/elements:

a feed line adapted for feeding fluid (dialysis fluid) from the internal fluidics to an extracorporeal blood conduit system/hose system (constituting external fluidics) including patient-side ports so as to compensate e.g. planned high fluid losses on the patient side and at least one coupling means which is fluid-connected to the feed line and is especially arranged or provided at the downstream end thereof so as to couple a hose line of the extracorporeal hose system to the feed line.

The coupling means is arranged at a machine front face of the extracorporeal blood treatment machine/dialysis machine accessible by the user, the dialysis machine including a drain line in order to drain fluid from the extracorporeal hose system during the operations intended to prepare or after-treat the machine such as priming, flushing the dialyzer or disconnecting a patient, especially to feed the fluid to a waste reservoir via the drain line, the dialysis machine having a cover/flap for covering the coupling means, when no hose line of the extracorporeal hose system (blood conduit system) is coupled to the coupling means, wherein a short-circuit of the line is formed when the cover/flap is closed, or in other words a sealed volume surrounding the coupling means is formed, especially a volume sealed against the environment is formed by which the feed line is fluid-connected to the drain line.

The feed line can especially be a dialysis fluid feed line by which dialysis fluid can be pumped from the dialysis fluid reservoir to the dialyzer or a substitution fluid feed line by which dialysis fluid as substitution fluid can be fed to the extracorporeal hose system. The drain line can in particular be a dialysis fluid drain by which dialysis fluid can be conveyed from the dialyzer to the waste reservoir or a drain line separate from the dialysis fluid drain by which fluid from the extracorporeal hose system can be supplied to the waste reservoir.

The cover can be operated by a user and is preferably arranged to be easily accessible for the user at the dialysis machine, especially at the casing thereof, for example at the machine front face. It may be in an open state or in a closed state. In the open state a hose line of the external fluidics can be arranged at the coupling means or be coupled thereto so that a flow path formed of the feed line (of the internal fluidics) and the hose line (of the external fluidics) is constituted. In the closed state no hose line is coupled to the coupling means and, respectively, cannot be coupled to the same. In the closed state the cover forms the sealed volume or a sealed compartment, for example by contacting the machine casing or the feed line and the drain line in a sealing manner. Inside the volume sealed with the cover the coupling means, the aperture of the feed line and the aperture of the drain line are provided. In other words, the sealed volume and, respectively, the sealed compartment is fluid-connected to the feed line as well as to the drain line. In this way, when the cover is closed, a flow path is formed which leads from the feed line opening into the closed compartment via the compartment sealed by the cover into the drain line. Via this flow path the internal fluidics of the dialysis machine can be rinsed, purified and/or disinfected very easily, efficiently and especially completely. By closing the cover a self-contained flow path is formed in the internal fluidics. The latter has to be purified and/or disinfected in the afore-mentioned manner completely or only in parts as desired or requested.

A dialysis fluid or a substitute in accordance with the present description is meant to be a physiological fluid which enters into contact with the patient or his/her blood. Therefore it has to be absolutely ensured that the fluid conveyed in the dialysis machine is sterile and pyrogen-free.

The known pumps and, respectively, conveying means of the dialysis machine can especially be gear-type pumps or diaphragm pumps. Instead of a substitution fluid pump, for example a proportional valve, especially including a flow meter, can be used as substitute conveying means by which fluid conveyed by the other pumps (the dialysis fluid pump, especially the dialysis fluid feed pump or the dialysis fluid drain pump) in the internal fluidics is branched off as substitution fluid to the respective desired extent.

According to an embodiment of the invention, the drain line can lead to the dialysis fluid drain (and from there to the waste reservoir) and can be fluid-connected. It can especially lead from the coupling means to the dialysis fluid drain so that inside the internal fluidics a flow path is or can be formed which leads from the coupling means via the drain line and the dialysis fluid drain to the waste reservoir. The fluid-communication between the drain line and the dialysis fluid drain may be disconnected by a shut-off valve. In this way, in the dialysis machine numerous flow paths can be formed, especially those forming a fluid communication between the external fluidics and the waste reservoir, for example for preparing and after-treating the dialysis machine. Such communication can be formed or switched of particular advantage without lines of the external fluidics connected or coupled to the coupling element pertaining to the substitution fluid feed line having to be re-plugged.

According to a further embodiment, the internal fluidics may have two substitution fluid feed lines each including a coupling means to connect the extracorporeal hose system. In this way either both substitution fluid feed lines or one of the substitution fluid feed lines can be connected to the external fluidics. Moreover, either both substitution fluid feed lines or one of the substitution fluid feed lines can be provided with shut-off or flow control valves as well as, where necessary, a separate substitution fluid pump so that the fluid flowing through the respective substitution fluid feed line is individually adjustable and/or controllable. One substitution fluid feed line can be used for a fluid connection upstream (pre-dilution) and the other substitution fluid feed line can be used for fluid connection downstream (post-dilution) of the dialyzer. In this way, the dialysis machine can be operated both for pre-dilution and for post-dilution. A mixed operation is further possible by conveying simultaneously via both substitution fluid feed lines (mixed dilution). A change between said operating modes as well as the setting thereof during therapy is possible at any time. It is especially preferred that a substitution fluid line, hereinafter referred to a substitution fluid main line, branches off the dialysis fluid feed line, the substitution fluid pump being arranged in said substitution main line which is divided into the afore-mentioned two substitution fluid feed lines downstream of the substitution fluid pump. The substitution fluid flow can be effectuated by only one pump, wherein the division of the substitution fluid flow to the substitution fluid feed lines downstream of the pump is performed with said flow control valves.

According to an embodiment, the internal fluidics may have two drain lines each including a coupling means for connecting the extracorporeal hose system. Both drain lines can be connected to the external fluidics via their respective coupling means. In addition, either both drain lines or one of the drain lines can be provided with shut-off or flow control valves so that the fluid flowing through the respective drain line can be individually set and/or controlled.

It is of particular advantage when the two drain lines are fluid-communicated. Between the drain lines and/or in either or in each drain line a shut-off valve or control valve may be arranged. It is advantageous in this embodiment that the flow through each drain line (and thus the flow through the dedicated coupling and the line of the external fluidics connected thereto) can be adjusted with the shut-off or control valve without a change of connection from the external fluidics and the internal fluidics being required.

In an embodiment the substitution fluid feed line and, respectively, either of or both substitution fluid feed lines can be fluid-communicated to the drain line. This communication is realized exclusively inside the internal fluidics and can be implemented especially via a separate line (also referred to as communication line) leading from the substitution fluid feed line to the drain line. Between the substitution fluid feed line and the drain line a shut-off valve or control valve may be arranged. In this embodiment, it is of particular advantage that via the communication line a communication from the substitution fluid feed line to the drain line and thus to the waste reservoir can be implemented, which communication is formed exclusively inside the internal fluidics. Hence it is possible, for example, to purify or to rinse the substitution fluid lines without external fluidics having to be connected or used for the rinsing operation. Therefore, the use of an otherwise common single-use product can be dispensed with.

Optionally, moreover an air separator may be arranged in the drain line and, respectively, in either or both drain lines.

In an embodiment of the invention, the cover by which the coupling means has to be covered can be in sealing contact with the machine front face in the closed state. In this way a flow volume surrounding the coupling means by which the latter is fluid-connected or fluid-connectable to the drain line is formed in an especially simple manner. The cover can be lockable especially in the close state and/or in the open state so that it is safely retained in the respective state and tightness of the flow path formed by the closed cover is ensured. Moreover, it can be biased especially into the closed state, in particular with a spring or a similar biasing element, so that inadvertent escape of fluid can be prevented.

In an embodiment, the substitution fluid pump can be arranged upstream of a branching to the coupling means and a control valve for selective control of pre-dilution and/or post-dilution can be used downstream of the branching in each substitution fluid feed line.

In an embodiment, in the substitution fluid feed line a pressure sensor and especially an inflow pressure sensor can be disposed. This is meant to be a pressure sensor which is in direct fluid contact and thus senses the pressure directly inside the fluid/in the liquid. Preferably, between the fluid and the pressure sensor an air volume may still be provided in which in the static case the same pressure is prevailing as inside the fluid: Since air is compressible, however, an oscillating pressure signal as present on the blood side can be attenuated in this way. Via said pressure sensor the pressure in the substitution fluid feed line and thus also the pressure in blood hoses of the external fluidics can be sensed. Said pressure sensors and, respectively, such arrangement of the pressure sensors help to improve the measuring accuracy of the pressure in the external fluidics compared to conventional sensors in which measurement is performed via an air column, as the attenuation of the signal by the air column is omitted. Hence, for example venous needle disconnection (VND) can be detected more easily than in the state of the art.

It is noted that the dialysis machine according to aspects of the invention basically facilitates bolus administration. For bolus administration of a physiological fluid or physiological solution, i.e. infusion of said fluid to the blood circulation of a patient, a short-term switch-off of the balancing system is necessary. As a consequence, the feed pump and the drain pump can be operated at different pumping rates. The difference of said pumping rates then corresponds to the bolus administration into the patient. It is noted that bolus administration can be used to determine the recirculation. The bolus administration causes dilution of the hematocrit as well as decrease of concentrations of uremic substances. In the case of recirculation in the arterial feed line of the external fluidics a variation of the hematocrit or a concentration of uremic substances is brought about, which results in a change of signal during monitoring of the dialysis efficiency, especially in the case of real-time monitoring, so that in this way recirculation can be concluded.

BRIEF DESCRIPTION OF THE DRAWINGS

The invention is best understood from the following detailed description when read in connection with the accompanying drawings. Included in the drawings are the following figures:

FIG. 10 shows a schematic of flow paths in a dialysis machine according to aspects of the invention for connecting a patient, FIG. 11 shows a schematic of flow paths in a dialysis machine according to aspects of the invention for re-infusing blood to a patient, FIG. 12 shows a schematic of alternative flow paths in a dialysis machine according to aspects of the invention for re-infusing blood to a patient, FIG. 13 shows a schematic of flow paths in a dialysis machine according to aspects of the invention for emptying the external fluidics after treatment, FIG. 14 shows a schematic of flow paths in a dialysis machine according to aspects of the invention for preparing the dialyzer for re-use.

DETAILED DESCRIPTION OF THE PREFERRED EMBODIMENTS

Figure 1:
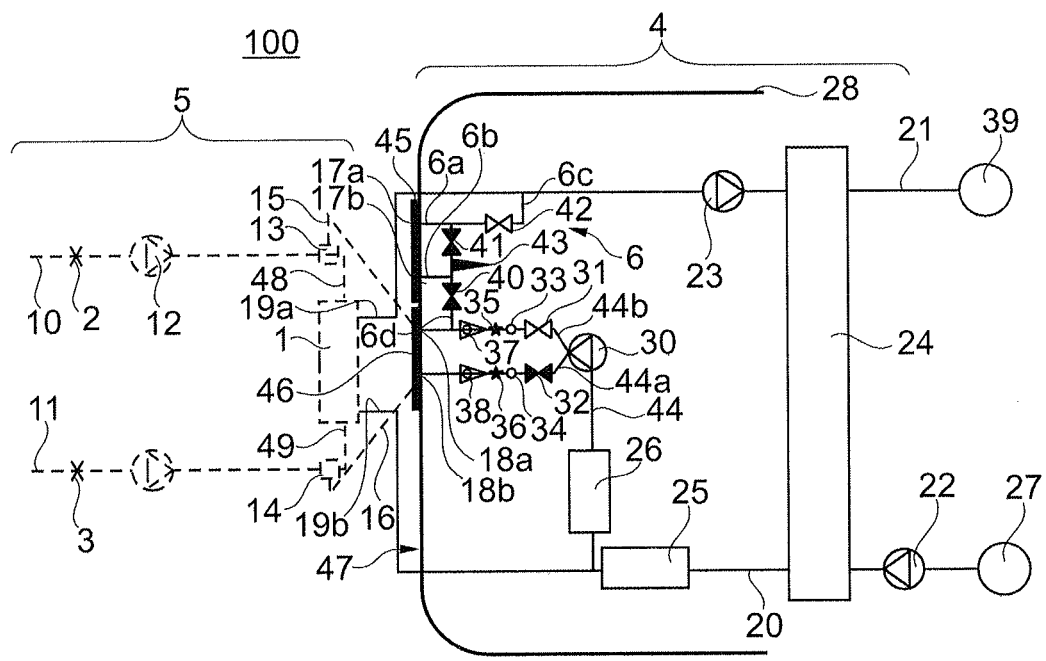
FIG. 1 shows a schematic of a first embodiment of a dialysis machine according to aspects of the invention.

FIG. 1 illustrates part of a first embodiment of a dialysis machine 100 according to aspects of the invention in a schematic. It includes internal fluidics 4 and external fluidics 5. The latter is generally also referred to as extracorporeal blood system or extracorporeal blood circulation and is shown in broken lines in the Figure.

The internal fluidics 4 is substantially completely accommodated in a machine casing 28 of the dialysis machine 100 schematically indicated in FIG. 1. It has a machine side or machine front face 47 which may be formed by the machine casing 28 and is accessible for a user, usually a patient or medical staff, for operating and handling the dialysis machine 100. The internal fluidics includes a dialysis fluid reservoir 27 and preferably a waste reservoir 39. With a dialysis fluid feed pump 22, hereinafter also referred to as feed pump 22, dialysis fluid is conveyed via a dialysis fluid feed line 19b, 20 to a dialyzer 1 usually arranged outside the machine casing 28. From there a dialysis fluid drain 19a, 21 leads to the waste reservoir 39. Dialysis fluid is pumped through the dialysis fluid drain 21 with a dialysis fluid drain pump 23, hereinafter also referred to as drain pump 23.

Dialysis fluid conveyed through the dialysis fluid feed line 20 and the dialysis fluid drain line 21 is detected and balanced by a balancing system 24 schematically indicated in FIG. 1.

The internal fluidics 4 includes a substitution fluid pump 30 by which part of the dialysis fluid flow conveyed through the dialysis fluid feed line 20 is branched off inside the machine and is passed to the external fluidics 5 through a substitution fluid feed line 44. The substitution fluid pump 30 is controlled by a computing unit not shown in the Figure which may be part of the balancing system 24, for example. In the dialysis fluid feed line 20 a filter 25 is arranged and in the substitution fluid line 44 a filter 26 is arranged.

Downstream of the substitution fluid pump 30 the substitution fluid feed line 44 is split into two substitution fluid feed lines 44a, 44b. In the shown circuitry with the external fluidics 5 the substitution fluid feed line 44a serves for feeding dialysis fluid post-dilution, while the substitution fluid feed line 44b serves for feeding dialysis fluid pre-dilution. According to the circuitry with the external fluidics 5, this can be reversed or can be vice versa. In the substitution fluid feed line 44a a control valve 32 for controlling the post-dilution is arranged downstream of the pump 30, followed by a pressure sensor 34, a red detector 36 for blood detection and a check valve 38. In the substitution fluid feed line 44b a control valve 31 for controlling the pre-dilution is arranged downstream of the pump 30, followed by a pressure sensor 33, a red detector 35 for blood detection and a check valve 37. It is noted that a proportional valve, especially one single proportional valve, can be employed instead of the valves 31 and 32. By controlling the valves 31, 32 internal to the machine there can be selected or changed between pre-dilution and post-dilution and, respectively, pre-bolus administration and post-bolus administration. Moreover, there is the option of a mixed dilution in which substitution and, respectively, bolus administration is performed pre and post. The connection or coupling between the substitution fluid feed lines 44a, 44b, on the one hand, and the external fluidics 5, on the other hand, will be described in the further course.

The internal fluidics 4 includes a drain line 6 which is provided separately from the dialysis fluid drain 21. In the shown embodiment, the drain line 6 substantially consists of two drain lines 6a and 6b as well as a drain line portion 6c. The drain lines 6a and 6b lead from ports or couplings 17a and 17b which are arranged at the machine front face 47 and will be described hereinafter in detail to the drain line portion 6c in which they are joined and from there to the dialysis fluid portion 21. In the drain line portion 6c a first drain valve 42 is arranged by which the entire drain line 6 can be shut off against the dialysis fluid drain 21. In the drain line 6b a second drain valve 41 is arranged by which the drain line 6b can be shut off against the drain line 6a and the drain line portion 6c, respectively. Upstream of the second drain valve 41 an air separator 43 is arranged.

The drain line 6 is connected to the substitution fluid feed line 44b via a connecting line 6d. The connecting line 6d can be considered part of the drain line 6. In the same a third drain valve 40 is arranged by which the connection between the substitution fluid feed line 44b, on the one hand, and the drain line 6 and, consequently, to the dialysis fluid drain 21 can be disconnected.

The external fluidics 5 used together with the dialysis machine 100 according to aspects of the invention is simple and is equal to numerous different therapies. By the illustrated external fluidics 5 the dialysis machine 100 can be used, for example, for hemodialysis (HD), hemofiltration (HF) or hemodiafiltration (HDF). Furthermore, process routines such as priming (rinsing the dialyzer at the beginning of therapy), flushing the dialyzer during therapy, filling the external fluidics with a patient's blood, substitution during HD, HF or HDF, bolus administration during therapy, measuring recirculation, re-infusing a patient's blood after therapy or preparing the dialyzer 1 for re-use can be carried out very easily and especially without changing the external fluidics 5. In addition, the external fluidics 5 can be easily emptied after treatment. It consists substantially of an arterial blood hose 48, a venous blood hose 49, a pre-feeding blood hose 15 and a post-feeding blood hose 16. The arterial blood hose 48 leads from an arterial port 10, through which it is connected to a patient, via a blood pump 12 to the dialyzer 1. The venous blood hose 49 leads from the dialyzer 1 to a venous port 11 through which it is connected to the patient. The arterial blood hose 48 has to be clamped with an arterial clamp 2. The venous blood hose 49 has to be clamped with a venous clamp 3.

The arterial blood hose 48 includes a pre-connector 13 between the blood pump 12 and the dialyzer 1. Via said pre-connector the pre-feeding blood hose 15 is fluid-communicated with the arterial blood hose 48 and thus also with the dialyzer 1. The venous blood hose 49 includes a post-connector 14 downstream of the dialyzer 1. Via said post-connector the post-feeding blood hose 16 is fluid-communicated with the venous blood hose 49 and thus also with the dialyzer 1. The connectors 13 and/or 14 can be in the form of an air bubble separator (venting means of a known design) for example at a pressure sensor of the external fluidics, as usually provided in such hose systems. A connection can also be provided via a T-member introduced to the arterial and, respectively, venous blood hose 48 and, respectively, 49.

A fluid flow, especially a blood flow, can be generated by the blood pump 12 from the arterial port 10 via the dialyzer 1 to the venous port 11. When the blood flows through the dialyzer 1, it is separated in a known manner by a semipermeable membrane not shown in the Figures and passed by the dialysis fluid which is supplied to the dialyzer 1 via the dialysis fluid feed line 20 and which is discharged from the dialyzer 1 via the dialysis fluid drain 21.

The coupling or connection between the internal fluidics and the external fluidics is provided via coupling means or couplings 17a, 7b, 18a, 18b. They are arranged at the machine front face 47 to be accessible and operable for a user and are illustrated in detail in various embodiments in FIG. 3, FIG. 4, FIG. 5, FIG. 15 and FIG. 16.

Figure 3:
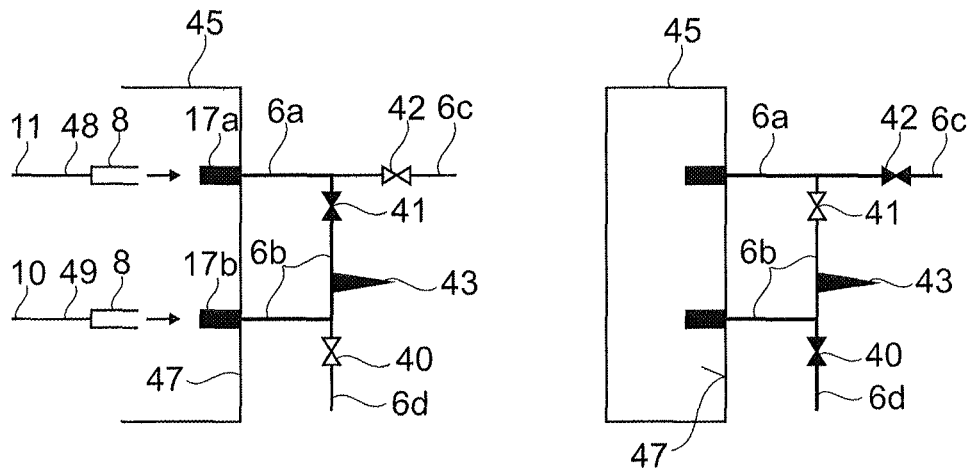
FIG. 3 shows a schematic of the coupling zone between the external fluidics and the internal fluidics in a configuration.
Figure 4:
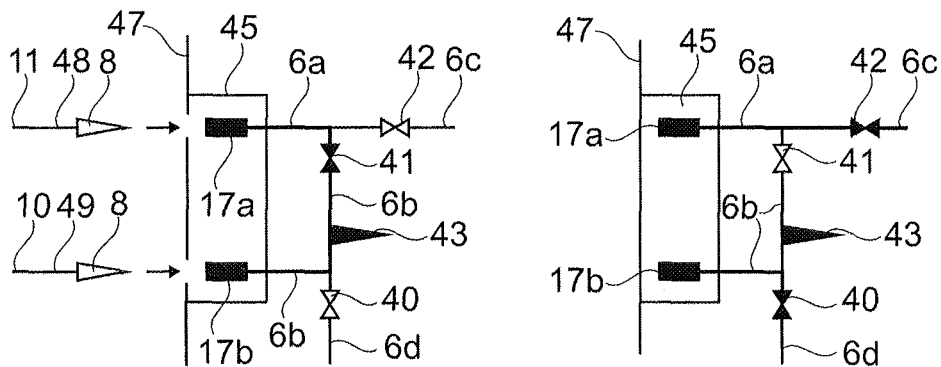
FIG. 4 shows a schematic of the coupling zone between the external fluidics and the internal fluidics in a configuration different from FIG. 3.

In the embodiment of FIG. 3 the coupling means or couplings 17a, 17b, 18a, 18b can be in the form of Luer locks, "small-bore connectors" or the like. The couplings 17a, 17b, 18a, 18b of FIG. 3 are arranged on the machine front face 47 and are raised with respect to the latter. In the embodiment of FIG. 4 the coupling means or couplings 17a, 17b, 18a, 18b can be in the form of pin connectors. In this embodiment, an indentation or recess 66 in which the couplings 17a, 17b, 18a, 18b are disposed is formed in the machine front face 47 in the area of the couplings 17a, 17b, 18a, 18b.

A rinsing flap 45 (for the couplings 17a and 17b of the drain line 6) and a rinsing flap 46 (for the couplings 18a and 18b of the substitution fluid lines 44a, 44b) are provided e.g. at the machine front face 47. Each of the rinsing flaps 45, 46 constitutes a cover 45 and, respectively, 46 for the couplings 17a, 17b and the couplings 18a, 18b, respectively. They can be brought into a respective opened position/opened state and a respective closed position/closed state. In the opened position accessibility to the couplings 17a, 17b, 18a, 18b is given for connecting the external fluidics 5, especially the arterial blood hose 48, the venous blood hose 49, the pre-feeding blood hose 15 and the post-feeding blood hose 16, depending on the type of therapy to be carried out. The rinsing flap 45 is illustrated in the left-hand picture of FIG. 3 and, respectively, FIG. 4 in the opened state and in the right-hand picture of FIG. 3 and, respectively, FIG. 4 in the closed state.

In the closed state each of the rinsing flaps 45, 46 forms a sealed volume around the respective couplings 17a, 17b, 18a, 18b, for example as they are in sealing contact with the machine front face 47 or with the couplings 17a, 17b, 18a, 18b themselves. When the rinsing flap 45 is closed, the couplings 17a and 17b are accommodated in the volume sealed with the rinsing flap 45. When the rinsing flap 46 is closed, the couplings 18a and 18b are accommodated in the volume sealed with the rinsing flap 46. In other words, with the rinsing flap 45 being closed, an outwardly sealed flow path (short-circuit) is formed which leads from the drain line 6b via the coupling 17b into the volume sealed by the closed rinsing flap 45 and from there via the coupling 17a to the drain line 6a. In the same way, with the rinsing flap 46 being closed, an outwardly sealed flow path (short-circuit) is formed which leads from the substitution fluid feed line 44a via the coupling 18b into the volume sealed by the closed rinsing flap 46 and from there via the coupling 18a to the substitution fluid feed line 44b.

Figure 2:
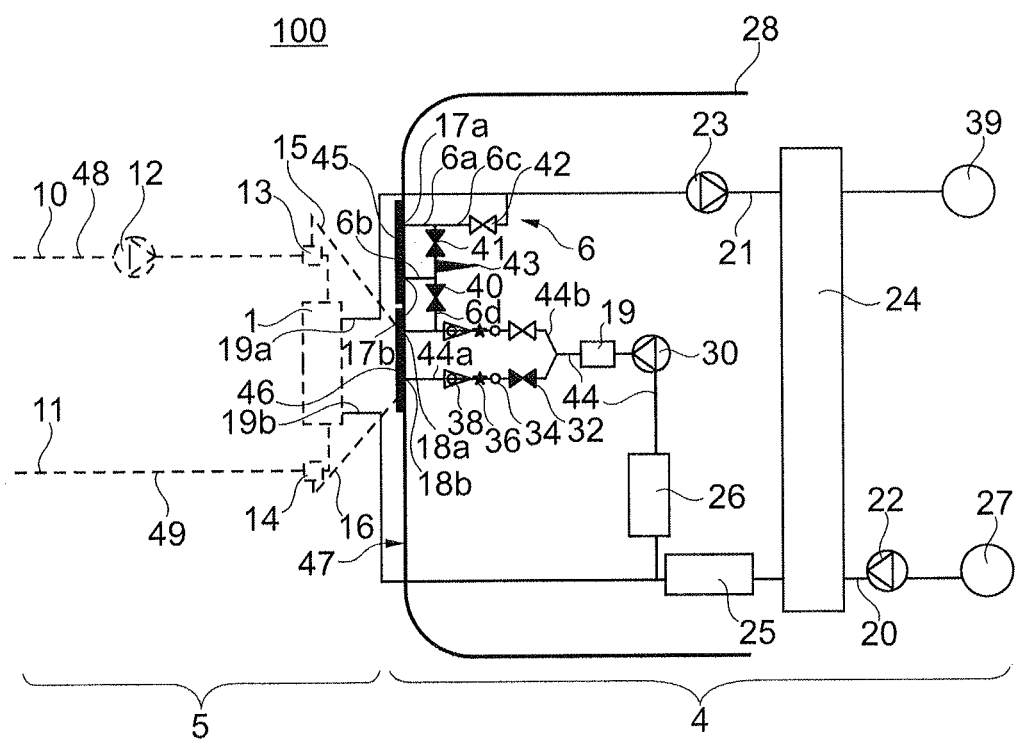
FIG. 2 shows a schematic of a second embodiment of a dialysis machine according to aspects of the invention.

The embodiment of the dialysis machine 100 shown in FIG. 2 differs from the embodiment illustrated in FIG. 1 by a further filter 19 arranged downstream of the substitution fluid pump 30 in the substitution fluid line 44. The filter 19 serves for protecting the patient from particles. It may be, but need not be, identical to the filters 25, 26 and provided additionally or alternatively to the latter or either of the latter. Otherwise the description of the embodiment of FIG. 1 is referred to.

Figure 5:
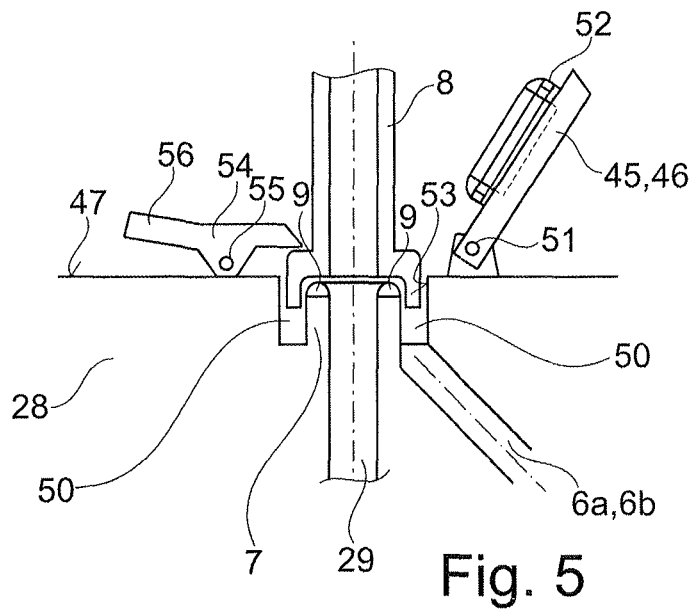
FIG. 5 shows a sectional view of a coupling between the internal fluidics and the external fluidics.

An embodiment of a coupling 17a, 17b, 18a, 18b which can be utilized alternatively or additionally to the aforedescribed embodiments is shown in detail in FIG. 5 by a schematic sectional view. The machine casing 28 including the machine front face 47 is visible. At least one end portion of a feed line 29 is introduced to the machine casing. The feed line 29 shown in FIG. 5 can be one of the substitution fluid lines 44a, 44b or one of the drain lines 6a, 6b. The end of the feed line 29 at the machine front side is configured to form a coupling element 7 as coupling or coupling means 17a, 17b, 18a, 18b to which one of the hose lines 15, 16, 48, 49 of the external fluidics 5 can be coupled with a matching connector 8. A seal 9 is arranged between the coupling element 7 and the connector 8. The coupling element 7 is surrounded by an annular channel 50 into which a drain line 6, 6a, 6b opens. At the machine front face 47 a cover 45, 46 pivoting about a hinge 51 is arranged next to the annular channel 50. At an outer edge the cover includes an O-ring seal 52 which seals against an outer wall 53 of the annular channel 50 when the cover 45, 46 is closed. In FIG. 5 the cover 45, 46 is shown in an opened position. The external fluidics 5 is connected to the feed line 29 in that the connector 8 connected to a hose line 15, 16, 48, 49 of the external fluidics 5 is slipped onto the coupling element 7 and sealed with the seal 9. The connector 8 is retained at the coupling element 7 by the action of a detent 54. The latter is pivoting about an axle 55 and is biased into the shown position by a spring bias so that the connector 8 is forced onto the coupling element 7 and against the seal 9 with the detent 54. For releasing the connector 8 the detent 54 is actuated via a lever 56 and in this way pivoted about the axle 55. As a consequence, the detent 54 releases the connector 8 which then can be removed from the coupling element 7.

For forming a short-circuit flow path from the feed line 29 into the drain line 6, 6a, 6b, the sealing flap or cover 45, 46 is pivoted about its hinge 51 in the direction of the machine front face, until the seal 52 engages in the annular channel 50 and is in sealing contact with the wall 53 thereof. In this closed position the cover 45, 46 is retained and secured with the detent 54 in the same way as afore-described regarding the connector 8 and can only be released and opened by actuating the detent 54. The cover 45, 46 closed and sealed against the machine casing 28 forms a sealed volume surrounding the coupling element 7 into which the feed line 29 opens and from which the drain line 6, 6a, 6b leads away. In this way purification and disinfection of the feed line together with the coupling are easily and efficiently possible.

Figure 15:
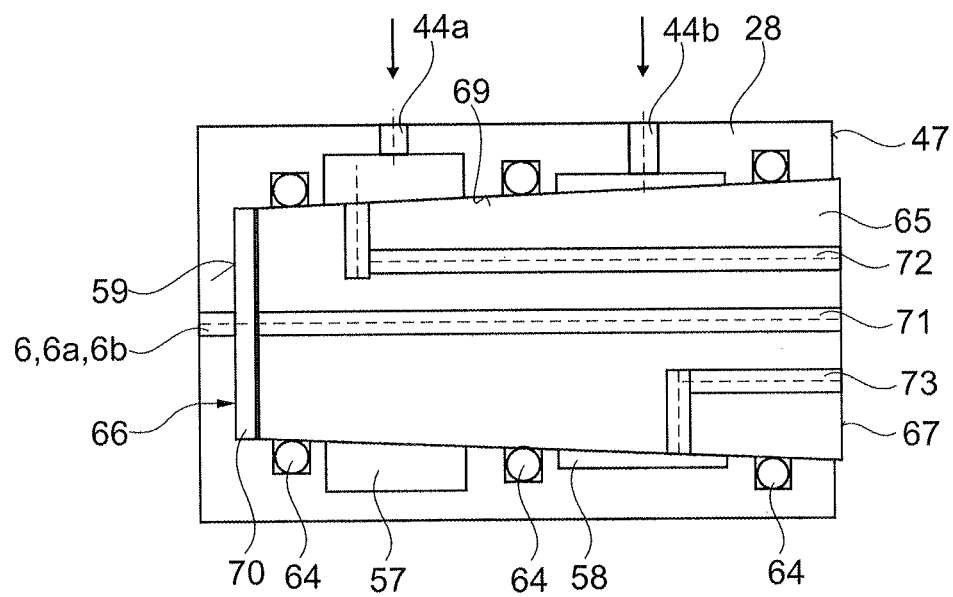
FIG. 15 shows a schematic sectional view of another option according to aspects of the invention for coupling external fluidics to internal fluidics.

Another embodiment of the coupling between the external fluidics 5 and the internal fluidics 4 is shown in FIG. 15. In this embodiment a substantially truncated indentation or recess 66 into which a first substitution fluid feed line 44a, a second substitution fluid feed line 44b and a drain line 6, 6a, 6b open out is introduced to the machine casing 28. A first ring channel 57 and a second ring channel 58 are introduced to the recess. The ring channels 57, 58 are formed in the circumferential surface 69 of the recess 66 and are fully circumferential in the same. The substitution fluid feed line 44a opens into the first ring channel 57. The substitution fluid feed line 44b opens into the second ring channel 58. The drain line 6, 6a, 6b opens into the end face 59 of the recess 66. Respective O-ring seals 64 are arranged between the end face 59, the first ring channel 57 and the second ring channel 58. At the machine front face 47 a cover 45, 46 may be arranged in the way as afore-described with respect to FIG. 5, although this is not shown in FIG. 15.

Into the recess 66 of the machine casing 28 a connecting adapter 65 in the form of plug-connector is introduced. It is arranged and configured especially for use together with a dialysis machine according to aspects of the invention. It consists preferably of plastic material and can be manufactured especially by injection molding. It exhibits an outer contour corresponding to the circumferential surface 69 of the recess 66, especially a truncated outer contour. The connector 65 is sealed against the circumferential surface 69 of the recess 66 with the O-ring seals 64. The diameter of the connector 65 can be configured so that the latter cannot be inserted against the end face 59 into the recess 66 but that a cavity 70 is retained between the end face 59 and the connector 65.

The connector 65 is provided with continuous channels 71, 72, 73. The channel 71 leads from a front side 67 of the connector 65 to the end face 68 thereof which is opposed to the end face 59 of the recess 66. The channels 72 and 73 are formed by intersecting bores and lead from the front side 67 of the connector 65 to the circumferential surface thereof, namely in the area of the annular channels 57, 58. The openings of the channels 71, 72 and 73 on the front side 67 of the connector 65 are fluid-connected in the desired way to a line or a hose of the extracorporeal blood system (of the external fluidics 5); this is not shown in FIG. 15. By inserting the connector 65 into the recess 66 a fluid-communication is produced between the internal fluidics 4 and the external fluidics 5, wherein a first flow path (from the drain line 6 via the cavity 70 and the channel 71), a second flow path (from the dialysis fluid feed line 44a via the annular channel 57 and the channel 72) and a third flow path (from the dialysis fluid feed line 44b via the annular channel 58 and the channel 73) are formed with one single plug-connection. Said three flow paths are sealed against each other with the O-ring seals 64. As the connecting adapter 65 is removed and the flap 45, 46 (not shown in FIG. 15) which seals the recess or indentation 66 against the environment is closed, the two feed lines 44a, 44b and the drain line 6 can be purified and disinfected in the afore-described manner.

Figure 16:
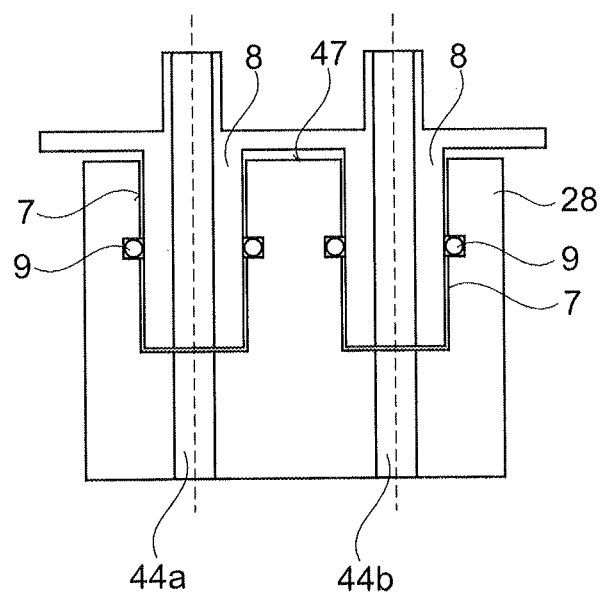
FIG. 16 shows a schematic sectional view of another coupling of external fluidics to internal fluidics according to aspects of the invention.

Another coupling according to aspects of the invention is illustrated in FIG. 16. It corresponds substantially to the coupling according to FIG. 4, but it is not brought about by individual connectors 8 but via a double connector. The latter includes two connectors 8 interconnected with a plate. The external fluidics 5 is connected to the internal fluidics 4 by the connectors 8 being inserted in couplings 7. Sealing is carried out via O-ring seals 9.

By the invention the external fluidics 5 can be connected in different ways to the dialysis machine 100 as shown in FIGS. 1 and 2. Exemplary connecting options are schematically illustrated in FIGS. 6 to 14 and will be explained hereinafter. For reasons of better clarity, in FIGS. 6 to 14 not all components of the dialysis machine 100 are shown and/or marked.

Figure 6:
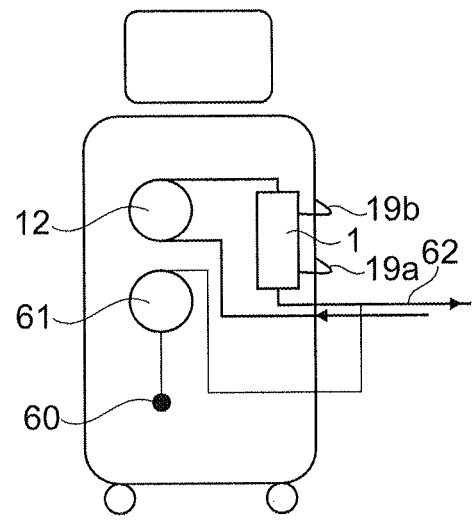
FIG. 6 shows a schematic of state-of-the-art flow paths for post-dilution.

FIG. 6 shows the flow path for a HDF including post-dilution in a conventional dialysis machine as known from the state of the art. Next to the blood pump 12, a separate substitution fluid pump 61 equally accessible for a user is arranged at the machine front face 47. Substitution fluid is fed from a separate substitution fluid access 60 with the substitution fluid pump 61 through a substitution fluid hose 63 of a connection 62 and is introduced to the extracorporeal blood circulation 5 there. The substitution fluid hose 63 is part of the external fluidics 5 and must be provided and present in different configurations and connections depending on the therapy to be applied.

Figure 7:
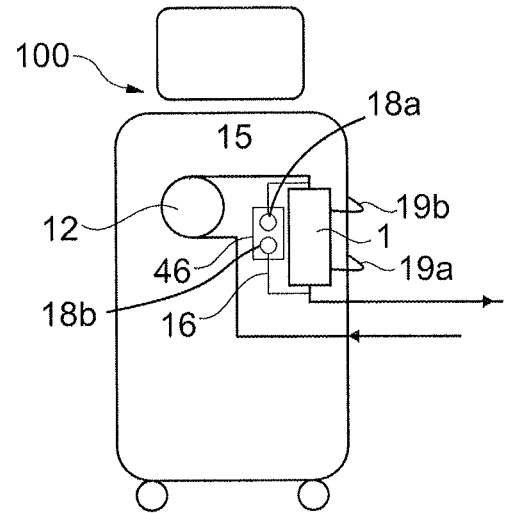
FIG. 7 shows a schematic of flow paths in a dialysis machine according to aspects of the invention during therapy.

FIG. 7 illustrates the flow path in a dialysis machine 100 according to aspects of the invention during therapy, wherein the external fluidics 5 is connected to the blood circulation of a patient not shown in the figure with the arterial port 10 and the venous port 11. In contrast to FIG. 6, the substitution fluid pump 61, the substitution fluid hose 63 and the connection 62 are omitted. Out of the parts of the external fluidics 5 the arterial blood hose 48 including the arterial port 10, the venous blood hose 49 including the venous port 11, the pre-feeding blood hose 15 and the post-feeding blood hose 16 as well as the blood pump 12 are shown. The shown connections permit pre-dilution and post-dilution and replace the previously required connections to the individual pressure sensors.

Figure 8:
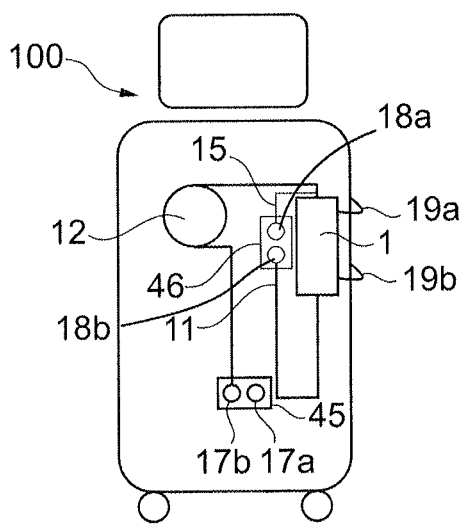
FIG. 8 shows a schematic of flow paths in a dialysis machine according to aspects of the invention during rinsing the dialyzer.

FIG. 8 illustrates the flow path in a dialysis machine 100 according to aspects of the invention during rinsing the dialyzer 1 and, respectively, for filling the external fluidics 5 with physiological fluid. Accordingly, rinsing fluid (physiological solution) is introduced via the substitution fluid line 44a and the coupling 18a into the post-feed line 16 upstream of the venous port 11 and into the venous part of the external fluidics 5. The rinsing fluid flows through the dialyzer 1 from the bottom to the top (in other words from the venous part into the arterial part), i.e. inversely to the common direction of flow during treatment. This flow with rinsing fluid is produced by the reversing blood pump 12. After flowing through the blood pump 12 the rinsing fluid is supplied via the arterial blood hose 48, whose arterial port 10 is coupled to the coupling 17b, to the drain line 6 and is guided via the latter into the waste reservoir 39. During such rinsing operation air is removed from the external fluidics 5 with the air separator 43.

Figure 9:
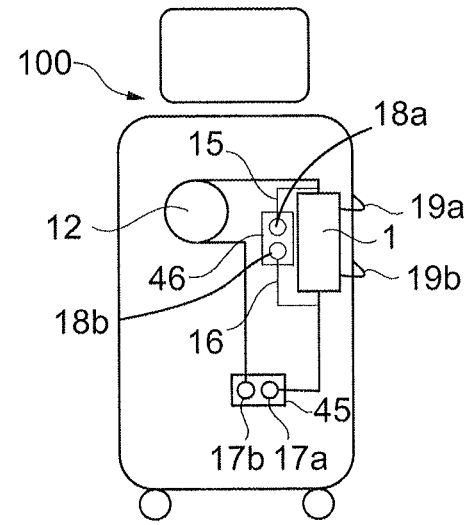
FIG. 9 shows a schematic of alternative flow paths in a dialysis machine according to aspects of the invention during rinsing the dialyzer.

FIG. 9 illustrates an alternative flow path in a dialysis machine 100 according to aspects of the invention during rinsing of the dialyzer 1 and, respectively, for filling the external fluidics 5 with physiological fluid. The venous blood hose 49 is connected to the coupling 17a by its venous port 11. The arterial blood hose 48 is connected to the coupling 17b by its arterial port 10. When the blood pump 10 does not pump and the venous clamp 3 is opened, the venous blood hose 49 is filled with rinsing fluid (physiological fluid) via the connector 14 (see FIG. 1, 2) in the direction of the venous port 11. Accordingly, air present in the venous blood hose 49 is conveyed into the drain line 6 and removed from the system. When the venous blood hose 49 is completely filled, the venous clamp 3 is closed. The blood pump 12 is operated against the usual pumping direction. In this way the dialyzer 1 and the other external fluidics 5, especially the arterial blood hose 48, are filled with rinsing fluid. Venting is equally performed via the air separator 43. When both hose areas, i.e. the arterial blood hose and the venous blood hose, are vented, the rinsing fluid is circulated via the short-circuited couplings 17a and 17b until a patient is connected to the system.

It is possible with this flow path that via the connector 14 (cf. FIGS. 1, 2) fluid is introduced to the system having a larger volume flow than the volume flow pumped by the blood pump 12 in reverse operation. A difference in volume flow that cannot be pumped by the blood pump 12 in reverse operation in this case flows via the venous blood hose 49 to the coupling 17a. In this way, of the venous blood hose 49 and the arterial blood hose 48 can be synchronously vented and filled.

FIG. 10 illustrates a flow path in a dialysis machine 100 according to aspects of the invention when a patient (not shown) is connected. This flow path can be arranged or implemented especially after filling and/or rinsing through one of the flow paths of FIGS. 8 and 9. Blood of the patient is pumped with the forwardly operated blood pump 12 through the arterial port 10 into the arterial blood hose 48 of the external fluidics. As blood flows into the external fluidics 5, the physiological fluid provided in the same is displaced and is conveyed through the coupling 17b into the drain line 6 and from there into the waste reservoir. In the area of the venous clamp 3 a red detector may be arranged in the venous blood hose 49. Preferably the red-detector is used to detect the time at which blood of the patient arrives at the clamp 3 and the venous blood hose 49 is to be connected to the patient's blood circulation by the venous port 11.

It is noted that, for the purpose of connecting a patient in a volume-stable manner, an immediate change can take place from the flow path for rinsing and/or filling the external fluidics 5 shown in FIG. 9 to the flow path shown in FIG. 7 for the patient's therapy.

FIG. 11 illustrates a flow path in a dialysis machine 100 according to aspects of the invention, when blood is re-infused to the blood circulation of a patient (not shown) after treatment. Accordingly, the arterial blood hose 48 is uncoupled from the patient's blood circulation and is attached to the coupling 18b. Physiological fluid present in the external fluidics 5 is then conveyed via the coupling 18b to the arterial port 10 into the arterial blood hose 48. Alternatively or additionally, physiological fluid can be conveyed via the coupling 18a into the pre-feed line 15 of the external fluidics 5 and from there via the connector 13 into the arterial blood hose 48. Moreover, it is possible to convey physiological fluid via the coupling 18b into the post-feed line 16 of the external fluidics 5 and from there via the connector 14 into the venous blood hose 49. As physiological fluid is introduced to the external fluidics 5, blood present therein is urged back into the patient's blood circuit.

FIG. 12 shows an alternative flow path in a dialysis machine 100 according to aspects of the invention for re-infusing blood after treatment into the blood circulation of a patient (not shown). The arterial port 10 is opened toward the atmosphere by opening the arterial clamp 2. Then air from the atmosphere is pumped into the arterial blood hose 48 with the blood pump 12. When the air reaches the connector 13, the conveying of the blood pump 12 is stopped. After that, physiological fluid is conveyed via the coupling 18a from the internal fluidics 4 via the pre-feed line and the connector 13 into the external fluidics 5, thus causing blood to be urged back therefrom into the patient's blood circulation in the afore-described way.

FIG. 13 illustrates a flow path in a dialysis machine 100 according to aspects of the invention for emptying the external fluidics 5 after re-infusing blood into the blood circulation of a patient (not shown). In the illustrated manner it is possible to completely empty the entire external fluidics 5. Thus the weight thereof as well as the costs for disposal are reduced. The arterial port 10 is opened toward the atmosphere by opening the arterial clamp 2. The venous port 11 is attached to the coupling 17a. Physiological fluid present in the external fluidics 5 as well as in the drain line 6 is pumped into the waste reservoir 39 with the dialysis fluid drain pump 23.

FIG. 14 illustrates a flow path in a dialysis machine 100 according to aspects of the invention for preparing the dialyzer 1 during disinfection for re-use. Accordingly, the arterial port 10 is attached to the coupling 17b. The venous port 11 is attached to the coupling 17a. In this flow path a disinfection fluid flows either through the coupling 18b via the dialyzer 1 and the reversing blood pump to the coupling 17b and from there via the drain line 6 to the waste reservoir 39 or through the coupling 18a via the dialyzer 1 to the coupling 17a. After disinfection, rinsing can take place through the same flow path with sterile water so as to remove the disinfectant from the dialyzer 1.

The invention claimed is:
1. A dialysis machine comprising internal fluidics, the internal fluidics including the following components:
    a dialysis fluid pump adapted to pump dialysis fluid from a dialysis fluid reservoir through a dialysis fluid feed line to a dialyzer and from the dialyzer through a dialysis fluid drain to a waste reservoir or to a waste line;
    a substitution fluid pump adapted to supply dialysis fluid through a substitution fluid feed line to an extracorporeal blood conduit system having patient-side ports;
    coupling means configured to connect the extracorporeal blood conduit system to the internal fluidics,
    the internal fluidics having a drain line comprising a first drain line and a second drain line running parallel to the first drain line;
    the internal fluidics further comprising a substitution fluid feed line comprising a first substitution fluid feed line and a second substitution fluid feed line running parallel to the first substitution fluid feed line;

the coupling means comprising coupling elements formed on each of the first drain line, second drain line, first substitution fluid feed line and second substitution fluid feed line, each coupling element configured to connect to the extracorporeal blood conduit system.

2. The dialysis machine according to claim 1, wherein the drain line also leads to the dialysis fluid drain.

3. The dialysis machine according to claim 1, wherein the first drain line and the second drain line fluid-communicate via a shut-off valve.

4. The dialysis machine according to claim 1, wherein the substitution fluid feed line fluid-communicates with the drain line via a shut-off valve.

5. The dialysis machine according to claim 1, wherein an air separator is arranged in the drain line.

6. The dialysis machine according to claim 1, wherein the substitution fluid pump is arranged upstream of a branch to the coupling means, and wherein a control valve is arranged downstream of the branch for selectively controlling at least one of pre-dilution or post-dilution and is employed in each substitution fluid feed line.

7. A dialysis machine comprising:
a hollow casing including internal fluidics inside the hollow casing, the internal fluidics including the following components:
  a dialysis fluid pump adapted to pump dialysis fluid from a dialysis fluid reservoir through a feed line to a dialyzer and from the dialyzer through a dialysis fluid drain to a waste reservoir or to a waste line,
  a substitution fluid line branching off from the feed line for feeding dialysis fluid from the internal fluidics to an extracorporeal blood conduit system including patient-side ports, at least one first coupling means arranged on a side of the hollow casing of the dialysis machine and between the extracorporeal blood conduit system and the substitution fluid line, wherein the at least one first coupling means is in fluid communication with the substitution fluid line so as to couple the extracorporeal blood conduit system to the substitution fluid line,
  a drain line having a second coupling means, the second coupling means configured to further connect the extracorporeal blood conduit system to the internal fluidics, wherein the drain line leads from the second coupling means to the waste reservoir or to the waste line, the drain line configured to drain fluid from the extracorporeal blood conduit system,
  a substitution fluid pump adapted to supply the dialysis fluid through the substitution fluid line to the extracorporeal blood conduit system;
  a first cover for the at least one first coupling means, the first cover positionable in an open state to provide access to the at least one first coupling means to connect the internal fluidics to the extracorporeal blood conduit system, and a closed state for covering the at least one first coupling means; and
  a second cover for the second coupling means, the second cover positionable in an open state to provide access to the second coupling means to connect the internal fluidics to the extracorporeal blood conduit system, and a closed state for covering the second coupling means;
wherein, when the first cover and the second cover are in their respective closed states, a sealed volume fluid-connection with the at least one first coupling means and the second coupling means of the drain line is formed, forming a short-circuit flow path through which the substitution fluid line is fluid-connected to the drain line.

8. The dialysis machine according to claim 7, wherein the drain line connects the extracorporeal blood conduit system to the waste reservoir.

9. The dialysis machine according to claim 7, wherein the cover in the closed state is in sealing contact with one casing side.

10. The dialysis machine according to claim 7, wherein the cover is a flap-type and is manually operable.

11. The dialysis machine according to claim 7, wherein the sealed volume surrounds the at least one first coupling means and the second coupling means of the drain line.

12. The dialysis machine according to claim 9, wherein the one casing side is a machine front face.

* * * * *